United States Patent
Tsuda

(10) Patent No.: US 8,197,126 B2
(45) Date of Patent: Jun. 12, 2012

(54) STIRRING DETERMINING DEVICE, STIRRING DETERMINING METHOD, AND ANALYZER

(75) Inventor: Nobuyoshi Tsuda, Hino (JP)

(73) Assignee: Beckman Coulter, Inc., Brea, CA (US)

( * ) Notice: Subject to any disclaimer, the term of this patent is extended or adjusted under 35 U.S.C. 154(b) by 113 days.

(21) Appl. No.: 12/687,644

(22) Filed: Jan. 14, 2010

(65) Prior Publication Data
US 2010/0135352 A1 Jun. 3, 2010

Related U.S. Application Data

(63) Continuation of application No. PCT/JP2008/062605, filed on Jul. 11, 2008.

(30) Foreign Application Priority Data

Jul. 18, 2007 (JP) .................................. 2007-187052

(51) Int. Cl.
*B08B 3/12* (2006.01)
*G01K 1/14* (2006.01)
*G01N 25/00* (2006.01)

(52) U.S. Cl. .............. 374/45; 374/141; 374/117; 134/1; 366/118

(58) Field of Classification Search .................. 374/4, 5, 374/7, 45, 57, 100, 110, 112, 115, 137, 166, 374/167, 164, 163, 183, 2, 9, 30, 208, 141–142, 374/117–119; 134/1, 88, 113, 166 C; 366/118
See application file for complete search history.

(56) References Cited

U.S. PATENT DOCUMENTS

| | | | | |
|---|---|---|---|---|
| 2,828,231 A * | 3/1958 | Henry | ................................ | 134/1 |
| 3,457,108 A * | 7/1969 | Hittel | ........................... | 134/22.1 |
| 3,507,695 A * | 4/1970 | Sawyer | ............................ | 134/1 |
| 5,024,744 A * | 6/1991 | Okabayashi | .................. | 204/194 |
| 5,226,969 A * | 7/1993 | Watanabe et al. | ................ | 134/7 |
| 5,716,458 A * | 2/1998 | Machino | ......................... | 134/42 |
| 5,853,489 A * | 12/1998 | Kitazawa | .......................... | 134/1 |
| 6,528,026 B2 * | 3/2003 | Hajduk et al. | ................ | 422/198 |
| 6,811,616 B2 * | 11/2004 | Wack | ............................. | 134/10 |
| 7,543,354 B2 * | 6/2009 | Lee et al. | ......................... | 15/302 |
| 2003/0190755 A1 * | 10/2003 | Turner et al. | .................... | 436/37 |
| 2007/0101533 A1 * | 5/2007 | Lee et al. | ........................ | 15/302 |
| 2009/0092518 A1 * | 4/2009 | Murakami | ................ | 422/82.05 |
| 2009/0165827 A1 * | 7/2009 | Kozy et al. | ................. | 134/22.12 |

FOREIGN PATENT DOCUMENTS

| | | | |
|---|---|---|---|
| CN | 101905985 A | * | 12/2010 |
| EP | 1 260 819 A1 | | 11/2002 |
| EP | 2 060 899 A1 | | 5/2009 |
| JP | 61274651 A | * | 12/1986 |
| JP | 2006-119125 A | | 5/2006 |
| WO | WO 01/63300 A1 | | 8/2001 |

OTHER PUBLICATIONS

English Translation International Search Report from PCT/JP2006/062605 dated Sep. 22, 2008 (3 pages in both English and Japanese).

* cited by examiner

*Primary Examiner* — Gail Verbitsky
(74) *Attorney, Agent, or Firm* — Kilpatrick Townsend & Stockton LLP

(57) ABSTRACT

A stirring determining device that determines whether stirring by a stirrer, which stirs liquid contained in a vessel using sound wave generated by a sound-wave generating unit that is attached to the vessel, is successful or unsuccessful. The stirring determining device includes a temperature sensor that measures a temperature of the liquid; and a determining unit that determines whether stirring of the liquid contained in the vessel is successful or unsuccessful depending on the temperature of the liquid measured at least before and after the stirring by the temperature sensor.

11 Claims, 10 Drawing Sheets

STIRRING DETERMINING DEVICE, STIRRING DETERMINING METHOD, AND ANALYZER

CROSS-REFERENCE TO RELATED APPLICATIONS

This application is a continuation of PCT international application Ser. No. PCT/JP2008/062605 filed on Jul. 11, 2008 which designates the United States, incorporated herein by reference, and which claims the benefit of priority from Japanese Patent Application No. 2007-187052, filed on Jul. 18, 2007, incorporated herein by reference.

BACKGROUND OF THE INVENTION

1. Field of the Invention

The present invention relates to a stirring determining device, a stirring determining method, and an analyzer.

2. Description of the Related Art

A stirrer that is used in an analyzer and stirs liquid contained in a vessel without making contact using a sound-wave generating element in order to prevent what is called carryover is conventionally known (for example, see Japanese Patent Application Laid-open No. 2006-119125). The stirrer stirs the liquid contained in the vessel using the sound wave generated by driving the sound-wave generating element.

SUMMARY OF THE INVENTION

A stirring determining device according to an aspect of the present invention determines whether stirring by a stirrer, which stirs liquid contained in a vessel using sound wave generated by a sound-wave generating unit that is attached to the vessel, is successful or unsuccessful, and includes a temperature sensor that measures a temperature of the liquid; and a determining unit that determines whether stirring of the liquid contained in the vessel is successful or unsuccessful depending on the temperature of the liquid measured at least before and after the stirring by the temperature sensor.

A stirring determining method according to another aspect of the present invention for determining whether stirring by a stirrer, which stirs liquid contained in a vessel using sound wave generated by a sound-wave generating unit, is successful or unsuccessful, includes a temperature measuring step of measuring a temperature of the liquid; and a determining step of determining whether stirring of the liquid contained in the vessel is successful or unsuccessful depending on the temperature of the liquid measured at least before and after the stirring.

An analyzer according to still another aspect of the present invention includes a stirrer that stirs liquid contained in a vessel using sound wave generated by a sound-wave generating unit attached to the vessel; and a stirring determining device that determines whether stirring by the stirrer is successful or unsuccessful, the stirring determining device including a temperature sensor that measures a temperature of the liquid; and a determining unit that determines whether stirring of the liquid contained in the vessel is successful or unsuccessful depending on the temperature of the liquid measured at least before and after the stirring by the temperature sensor.

The above and other features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

First Embodiment

Figure 1:
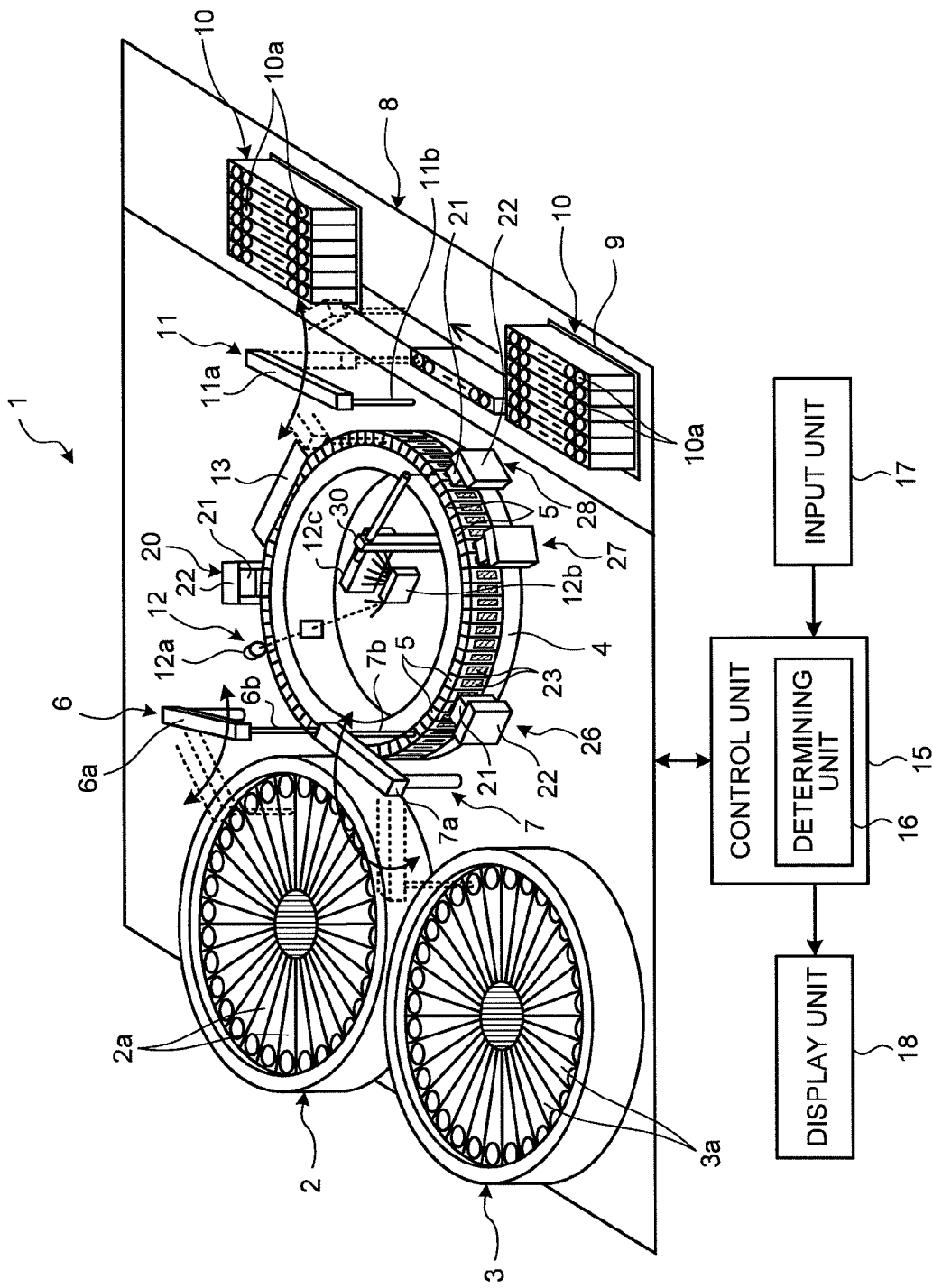
FIG. 1 is a schematic configuration diagram that illustrates an automatic analyzer according to a first embodiment.
Figure 2:
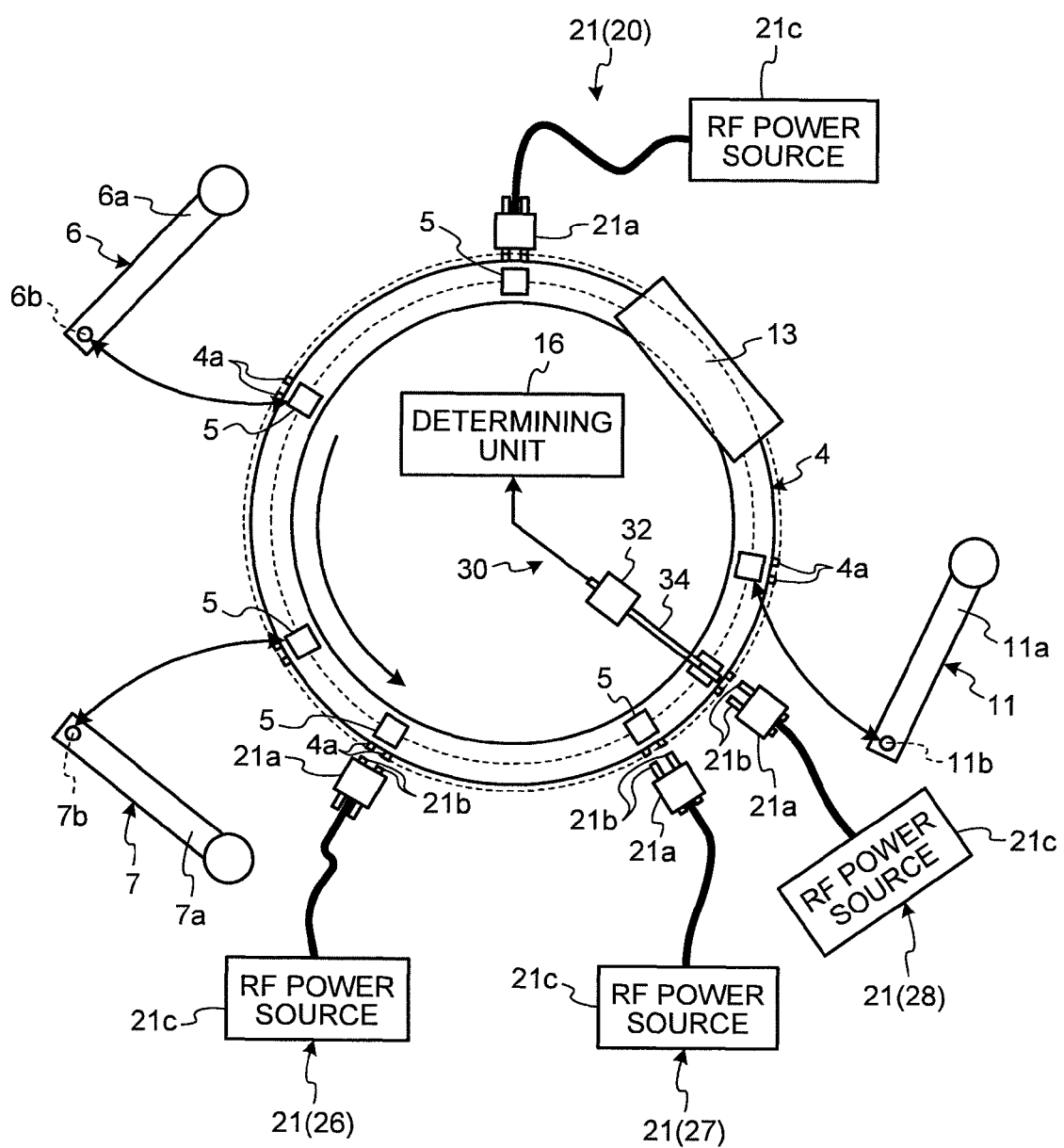
FIG. 2 is a plain view that illustrates reagent dispensing systems, a specimen dispensing system, a specimen stirrer, reagent stirrers, a determining stirrer, and a stirring determining device arranged near a reaction table in the automatic analyzer according to the first embodiment.

A detailed explanation will be given below of a first embodiment of a stirring determining device, a stirring determining method, and an analyzer according to the present invention with reference to the attached drawings. FIG. 1 is a schematic configuration diagram that illustrates an automatic analyzer according to the first embodiment. FIG. 2 is a plain view that illustrates reagent dispensing systems, a specimen dispensing system, a specimen stirrer, reagent stirrers, a determining stirrer, and a stirring determining device arranged near a reaction table in the automatic analyzer according to the first embodiment.

As depicted in FIGS. 1 and 2, an automatic analyzer 1 includes reagent tables 2, 3, a reaction table 4, a specimen-vessel transferring system 8, an analysis optical system 12, a cleaning system 13, a control unit 15, a specimen stirrer 20, reagent stirrers 26, 27, a determining stirrer 28, and a stirring determining device 30.

The reagent tables 2, 3 are rotated by respective driving means so as to transfer a reagent vessel 2a that contains a first reagent and a reagent vessel 3a that contains a second reagent in a circumferential direction as depicted in FIG. 1.

As depicted in FIGS. 1 and 2, a plurality of reaction vessels 5 is arranged on the reaction table 4 in a circumferential direction. The reaction table 4 is rotated while keeping the plurality of reaction vessels 5 at a predetermined temperature, for example, 37° C., and transfers the reaction vessels 5 in a circumferential direction. A plurality of connecting terminals 4a that establishes connections with sound-wave generating elements 23 is arranged on the outer surface of the reaction table 4, where each of the reaction vessels 5 is arranged, along a circumferential direction. The reaction table 4 rotates, for example, (one revolution subtracted by one reaction vessel)/4 revolution in one cycle, and rotates (one revolution subtracted by one reaction vessel) revolution through four cycles. The plurality of reaction vessels 5 arranged on the reaction table 4 is transferred in a circumferential direction due to the intermittent rotation of the reaction table 4. During the rotation, reagent dispensing, specimen dispensing, stirring of a liquid sample that includes a reagent and a specimen, optical measurement of a reagent, a specimen, and a reaction liquid, and cleaning are performed. Reagent dispensing systems 6, 7, a specimen dispensing system 11, the specimen stirrer 20, the reagent stirrers 26, 27, the determining stirrer 28, and the stirring determining device 30 are arranged near the reaction table 4.

The reaction vessel 5 is a cuvette whose capacity is very small, from several μL to several hundreds of μL, and a transparent material is used, through which more than 80% of light contained in the analysis light emitted by a light emitting unit 12a of the analysis optical system 12 is transmitted. For example, glass including heat-resistant glass or synthetic resin such as cyclic olefin and polystyrene may be used. The reaction vessel 5 has the sound-wave generating element 23 attached to a side wall 5a (see FIG. 4) and forms the stirrer 20 together with the sound-wave generating element 23. The reaction vessel 5 is arranged on the reaction table 4 such that the sound-wave generating element 23 faces outward in a radial direction. The first reagent and the second reagent are sequentially dispensed from the reagent vessels 2a, 3a by the reagent dispensing systems 6, 7 arranged near the outer circumference of the reaction table 4.

The reagent dispensing systems 6, 7 have respective probes 6b, 7b that dispense reagents and that are attached to respective arms 6a, 7a that are rotated in the directions indicated by arrows in a horizontal plane. The reagent dispensing systems include probe cleaning means that cleans the probes 6b, 7b using cleaning water.

As depicted in FIG. 1, the specimen-vessel transferring system 8 transfers a plurality of racks 10 arranged on a feeder 9 step by step in the direction indicated by an arrow. The rack 10 holds a plurality of specimen vessels 10a that contain specimens. Each time the step transfer of the rack 10 by the specimen-vessel transferring system 8 is stopped, the specimen contained in the specimen vessel 10a is dispensed in the reaction vessel 5 by the specimen dispensing system 11 that includes a drive arm 11a rotated in a horizontal direction and a probe 11b. The specimen dispensing system 11 includes a probe cleaning means that cleans the probe 11b using cleaning water.

The analysis optical system 12 emits analysis light to analyze liquid contained in the reaction vessel 5 where the reagent and the specimen are reacted. As depicted in FIG. 1, the analysis optical system includes the light emitting unit 12a, a light splitting unit 12b, and a light receiving unit 12c.

The analysis light emitted by the light emitting unit 12a is transmitted through the liquid contained in the reaction vessel 5 and is received by the light receiving unit 12c located at a position opposed to the light splitting unit 12b. The light receiving unit 12c is connected to the control unit 15 and outputs a light intensity signal of the received analysis light to the control unit 15.

Figure 3:
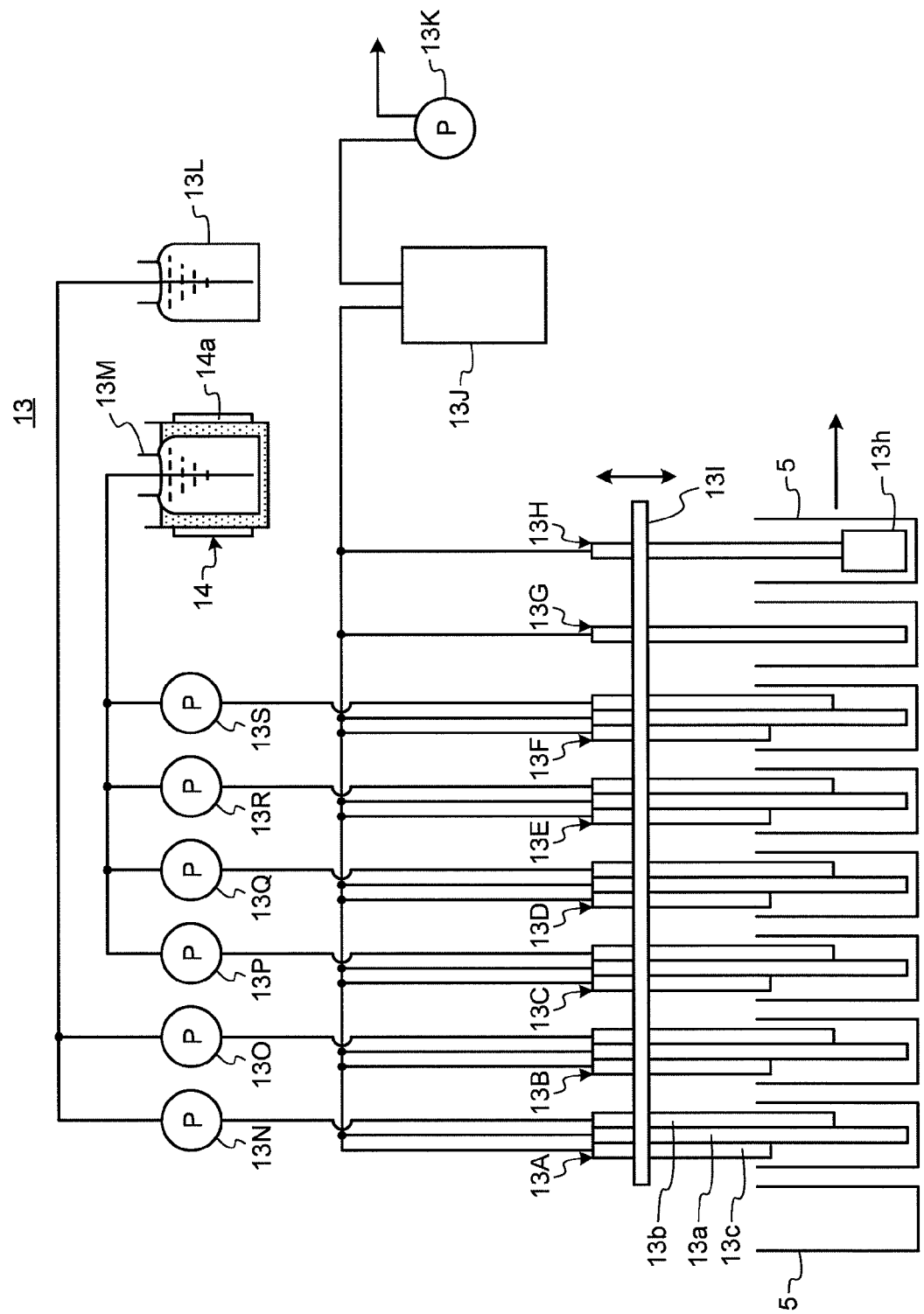
FIG. 3 is a schematic configuration diagram that illustrates a cleaning system used in the automatic analyzer depicted in FIG. 1.

The cleaning system 13 cleans the reaction vessel 5 after the optical measurement is finished. As depicted in FIG. 3, the system includes detergent nozzle pairs 13A, 13B, cleaning nozzle pairs 13C to 13F, suction nozzles 13G, 13H, a waste-liquid tank 13J, a detergent tank 13L, a cleaning-water tank 13M, and liquid sending pumps 13N to 13S that are connected via pipes. The cleaning system 13 sequentially cleans the reaction vessels 5 transferred due to the rotation of the reaction table 4 in the direction indicated by an arrow while moving up and down. The detergent nozzle pairs 13A, 13B, the cleaning nozzle pairs 13C to 13F, and the suction nozzles 13G, 13H are supported by a support member 13I and are moved up and down together by a driving means that drives the support member 13I.

Each of the detergent nozzle pairs 13A, 13B and the cleaning nozzle pairs 13C to 13F includes a suction nozzle 13a that is inserted into an area near the bottom of the reaction vessel 5, a dispensing nozzle 13b that is inserted into a middle area of the reaction vessel 5, and an overflow suction nozzle 13c that is inserted into an upper area of the reaction vessel 5. Each nozzle has a different length. The cleaning-water tank 13M is held in a constant-temperature water tank 14 in which a heater 14a is arranged, and the cleaning water is controlled at 35 to 45° C. The inside of the waste-liquid tank 13J is maintained at a negative pressure by a vacuum pump 13K.

The detergent nozzle pair 13A sucks up the reaction liquid contained in the reaction vessel 5 using the suction nozzle 13a, disposes of the reaction liquid into the waste-liquid tank 13J, and discharges the detergent contained in the detergent tank 13L into the reaction vessel 5 via the dispensing nozzle 13b using the liquid sending pump 13N. At that time, the overflow suction nozzle 13c sucks up excess detergent and disposes of the detergent into the waste-liquid tank 13J, thereby preventing the detergent from overflowing from the reaction vessel 5. The overflow suction nozzle 13c also prevents the overflow of the detergent or cleaning water for other nozzle pairs.

The detergent nozzle pair 13B sucks up the detergent discharged into the reaction vessel 5 by the detergent nozzle pair 13A using the suction nozzle 13a, disposes of the detergent into the waste-liquid tank 13J, and discharges the detergent contained in the detergent tank 13L into the reaction vessel 5 via the dispensing nozzle 13b using the liquid sending pump 13O.

The cleaning nozzle pair 13C sucks up the detergent discharged into the reaction vessel 5 by the detergent nozzle pair 13B using the suction nozzle 13a, disposes of the detergent into the waste-liquid tank 13J, and discharges the cleaning water contained in the cleaning-water tank 13M into the reaction vessel 5 via the dispensing nozzle 13b using the liquid sending pump 13P.

The cleaning nozzle pair 13D sucks up the cleaning water discharged into the reaction vessel 5 by the cleaning nozzle pair 13C using the suction nozzle 13a, disposes of the cleaning water into the waste-liquid tank 13J, and discharges the cleaning water contained in the cleaning-water tank 13M into the reaction vessel 5 via the dispensing nozzle 13b using the liquid sending pump 13Q. The same operation is repeatedly performed by the cleaning nozzle pairs 13E, 13F.

The cleaning nozzle pairs 13C to 13F suck up excess detergent or cleaning water using the overflow suction nozzle 13c so as to keep the cleaning water contained in the reaction vessel 5 at a certain amount. When the reaction vessel 5 with an inner bottom surface of 5×6 mm and a height of 30 mm is used, the reaction vessel 5 is set to contain 750 µL of cleaning water. This is set in consideration of the prevention of the overflow of the cleaning water due to the insertion of a temperature sensor 36 and a reasonable increase in the temperature of the cleaning water, which is a temperature measurement target, due to driving of the determining stirrer 28. The control unit 15 controls the cleaning nozzle pair 13F such that, when the cleaning water is used for determining whether the stirring is successful or unsuccessful, the amount of cleaning water supplied to the reaction vessel 5 from the dispensing nozzle 13b becomes smaller than the amount of cleaning water supplied to the reaction vessel 5 from the dispensing nozzles 13b of the cleaning nozzle pairs 13C to 13E upon cleaning.

The suction nozzle 13G sucks up the cleaning water discharged into the reaction vessel 5 by the cleaning nozzle pair 13F and disposes of the cleaning water into the waste-liquid tank 13J. The suction nozzle 13H has a chip 13h, which is made of a synthetic resin and attached to its lower end, sucks up the cleaning water left by the suction nozzle 13G, and disposes of the cleaning water into the waste-liquid tank 13J.

A microcomputer may be used for the control unit 15. The control unit 15 is connected to each component of the automatic analyzer 1. The control unit 15 controls the operation of each component and analyzes constituent concentrations and the like of a specimen on the basis of the absorbance of the liquid contained in the reaction vessel 5 in accordance with the intensity of light output from the light emitting unit 12a and the intensity of light received by the light receiving unit 12c. The control unit 15 causes an analysis operation to be performed while controlling the operation of each component of the automatic analyzer 1 in accordance with an analysis instruction input from an input unit 17, such as a keyboard. The control unit 15 displays on a display unit 18, such as a display panel, an analysis result, warning information, and various types of information in accordance with a display instruction input from the input unit 17.

Figure 4:
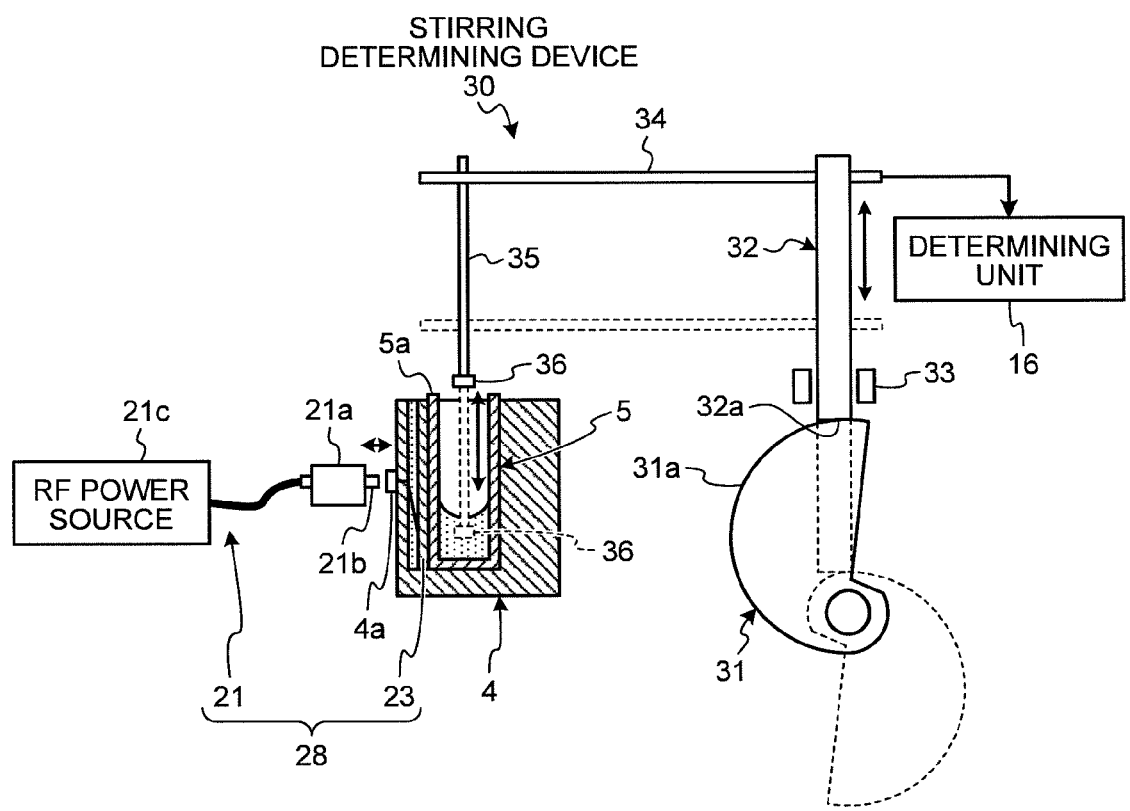
FIG. 4 is a diagram that illustrates the schematic configuration of the determining stirrer and the stirring determining device together with the cross-section surface of the reaction table that holds a reaction vessel.

The specimen stirrer 20, the reagent stirrers 26, 27, and the determining stirrer 28 perform noncontact stirring of liquid such as a specimen and a reagent contained in the reaction vessel 5 using sound wave generated by driving the sound-wave generating element 23. As depicted in FIGS. 1 and 4, the stirrer includes an electric-power transmitting member 21 and the sound-wave generating element 23. The determining stirrer 28 is a stirrer used for easily determining whether the stirring of the liquid is successful or unsuccessful in accordance with the degree of propagation of the sound wave generated by the sound-wave generating element 23 to the cleaning water contained in the reaction vessel 5. The determining stirrer has the same configuration as the specimen stirrer 20 and the reagent stirrers 26, 27. Therefore, an explanation will be given of the determining stirrer 28. Reference numerals that correspond to the corresponding components are used for the specimen stirrer 20 and the reagent stirrers 26, 27 so as to omit detailed explanations thereof.

The electric-power transmitting member 21 is arranged such that the electric-power transmitting member 21 is opposed to the reaction vessel 5 in a horizontal direction at a position where the electric-power transmitting member 21 and the outer circumference of the reaction table 4 are opposed to each other. The electric-power transmitting member 21 sends the electric power supplied from a high-frequency alternating-current source of about several MHz to several hundreds of MHz to the sound-wave generating element 23. As depicted in FIG. 2, the electric-power transmitting member 21 includes a solenoid 21a and a radio-frequency (RF) power source 21c as well as a driving circuit and a controller. As depicted in FIG. 4, the electric-power transmitting member 21 causes a connecting terminal 21b to be in contact with the connecting terminal 4a for the sound-wave generating element 23 arranged on the outer surface of the reaction table 4 using the solenoid 21a in order to drive the sound-wave generating element 23. As depicted in FIG. 1, the electric-power transmitting member 21 is supported by an arrangement determining member 22 and, when the rotation of the reaction table 4 is stopped, sends the electric power from the connecting terminal 21b to the connecting terminal 4a so that liquid, such as a specimen and a reagent, contained in the reaction vessel 5 is stirred by the sound wave generated by the sound-wave generating element 23.

Upon sending the electric power from the electric-power transmitting member 21 to the connecting terminal 4a, the arrangement determining member 22 moves the electric-power transmitting member 21 so as to adjust the relative arrangement of the electric-power transmitting member 21 and the connecting terminal 4a in the circumferential direction and the radial direction of the reaction table 4.

The sound-wave generating element 23 may be configured such that a oscillator formed of a plurality of comb-teeth electrodes (IDT) is arranged on one surface of a piezoelectric substrate made of lithium niobate (LiNbO3) and is attached to the side wall 5a (see FIG. 4) of the reaction vessel 5 via an acoustic matching layer such as an epoxy resin or an ultraviolet curable resin. If the sound-wave generating element 23 is driven at, for example, 1.6 W for about 2.4 seconds, the temperature of the 750 mL cleaning water, which is contained in the reaction vessel 5 and controlled at 35 to 45° C., is increased by about 1° C.

The stirring determining device 30 detects the degree of propagation of the sound wave generated by the sound-wave generating element 23 to the liquid contained in the reaction vessel 5 on the basis of an increase in the temperature of the liquid in order to determine whether the stirring of the liquid is successful or unsuccessful. As depicted in FIGS. 1, 2, and 4, the stirring determining device 30 is located at a position opposed to the determining stirrer 28 with the reaction table 4 interposed therebetween and includes a temperature sensor 36 and a determining unit 16. The stirring determining device 30 easily and reliably determines whether the propagation of the generated sound wave to the liquid contained in the reaction vessel 5 is successful or unsuccessful. The unsuccessful propagation is sometimes caused by poor adhesion of the sound-wave generating element 23 to the reaction vessel 5, separation of the sound-wave generating element 23 from the reaction vessel 5, adherence of water or an elastic material to the surface of the sound-wave generating element 23, or the like.

The temperature sensor 36 is provided at the lower end of a support member 35 and measures the temperature of the liquid contained in the reaction vessel 5. For example, a thermistor or a thermocouple is used. The support member 35 is supported by an arm 34 arranged on a support rod 32 that moves up and down due to the rotation of a cam 31. The cam 31 is rotated by a driving means such as an undepicted motor. A step portion 32a that is in contact with a cam surface 31a of the cam 31 is formed in the middle of the support rod 32, and a guide member 33 smoothly guides the up-and-down movement of the support rod 32 in accordance with the rotation of the cam 31.

The determining unit 16 is integrally formed with the control unit 15 and determines whether the stirring of the liquid contained in the reaction vessel 5 is successful or unsuccessful on the basis of the change in the temperature of the liquid, which has been measured by the temperature sensor 36, before and after the stirring.

The automatic analyzer 1 that has the configuration as described above is operated under the control of the control unit 15 so that the first reagent, the second reagent, and the specimen are sequentially dispensed by the reagent dispensing systems 6, 7 and the specimen dispensing system 11 in the plurality of reaction vessels 5 transferred by the rotating reaction table 4 in a circumferential direction. The dispensed reagents and specimen are sequentially stirred by the reagent stirrers 26, 27 and the specimen stirrer 20.

When the reaction vessel 5, in which the reagents and the specimen have been stirred, passes by the analysis optical system 12, the optical characteristics of the reaction liquid are measured by the light receiving unit 12c, and the constituent concentration or the like is analyzed by the control unit 15. The reaction vessel 5, for which the optical measurement of the reaction liquid is finished, is cleaned by the cleaning system 13 and then is used for analysis of a specimen again.

Before the analysis is started or after the analysis is finished, the automatic analyzer 1 determines, independently of the analysis operation, whether the stirring of the cleaning water is successful or unsuccessful using the sound wave generated by the sound-wave generating element 23. For example, the automatic analyzer 1 usually cleans reaction vessels 5 using the cleaning system 13 before the analysis is started, and, at that time, the automatic analyzer 1 detects the degree of propagation of the sound wave generated by the sound-wave generating element 23 to the cleaning water contained in the reaction vessel 5 on the basis of an increase in the temperature of the cleaning water. Thus, whether the stirring of the cleaning water due to the sound wave generated by the sound-wave generating element 23 is successful or unsuccessful can be easily and reliably determined using the stirring determining device 30.

Figure 5:
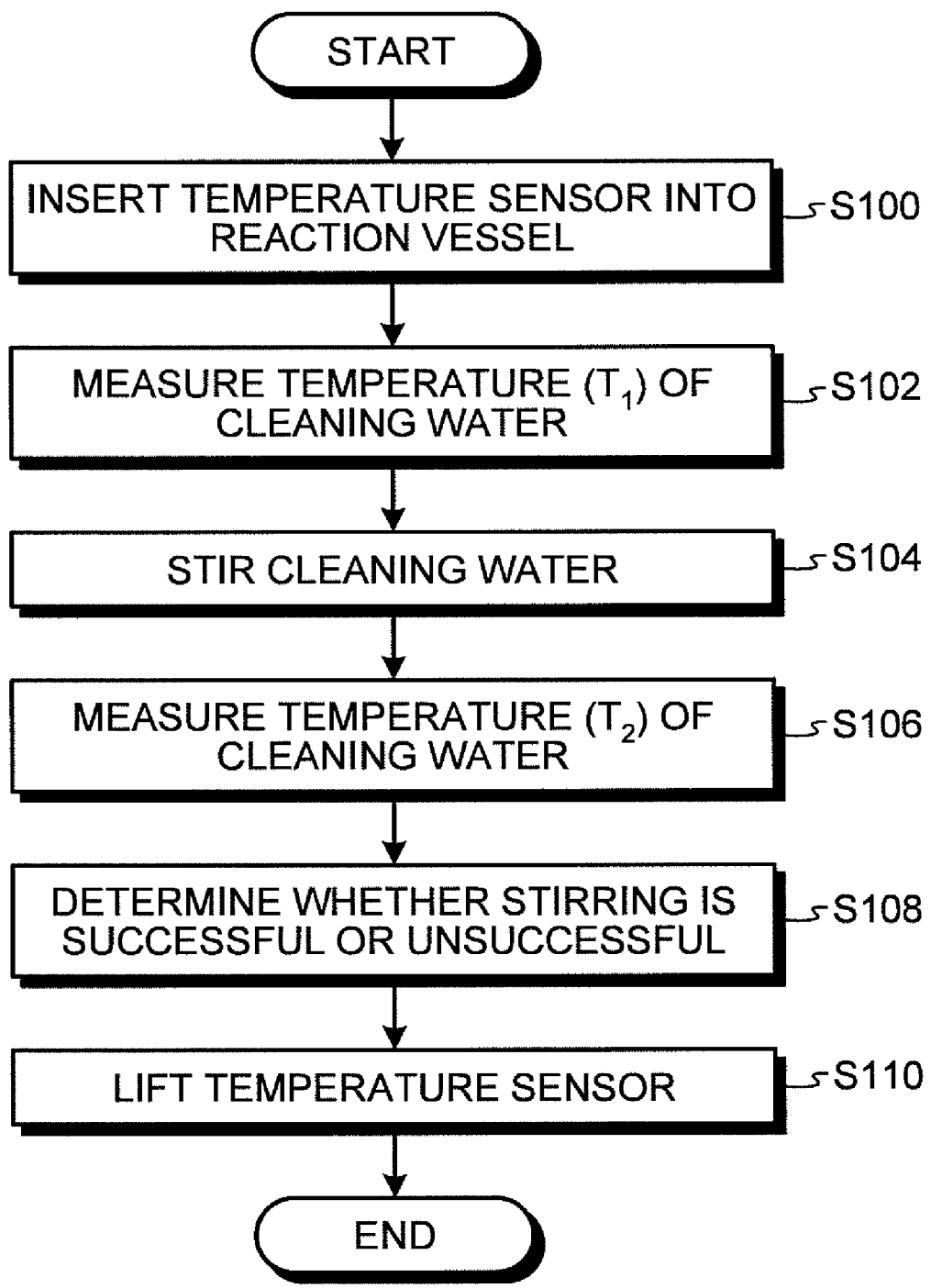
FIG. 5 is a flowchart that explains a procedure for determining whether the stirring of cleaning water using sound wave is successful or unsuccessful.

In that case, the control unit 15 causes the dispensing nozzle 13b of the cleaning nozzle pair 13F to discharge a certain amount of cleaning water into each reaction vessel 5 transferred to the position of the cleaning system 13 by rotating the reaction table 4 and then causes the support member 13I to raise the cleaning nozzle pair 13F together with the other nozzle pairs. Then, each of the reaction vessels 5 is sequentially transferred to the position of the determining stirrer 28 by rotating the reaction table 4, and it is determined whether the stirring of the cleaning water using sound wave is successful or unsuccessful. The cleaning water in the reaction vessel 5 after the measurement of a temperature (T2) is sucked up by the cleaning system 13. An explanation will be given below of the procedure for the successful/unsuccessful determination performed by the control unit 15 with reference to the flowchart depicted in FIG. 5.

First, the control unit 15 rotates the cam 31 of the stirring determining device 30 to move down the arm 34 to a predetermined position and inserts the temperature sensor 36 into the reaction vessel 5 (step S100). Next, the control unit 15 measures a temperature (T1) of the cleaning water in the reaction vessel 5 using the temperature signal input from the temperature sensor 36 (step S102). The control unit 15 outputs the measured temperature (T1) of the cleaning water to the determining unit 16.

Next, the control unit 15 drives the electric-power transmitting member 21 of the determining stirrer 28 so that the solenoid 21a causes the connecting terminal 21b to be in contact with the connecting terminal 4a for the sound-wave generating element 23 arranged on the outer surface of the reaction table 4. Thus, the control unit 15 drives the sound-wave generating element 23 for a certain period of time to stir the cleaning water (step S104). The sound-wave generating element 23 is driven, for example, for one second.

Figure 6:
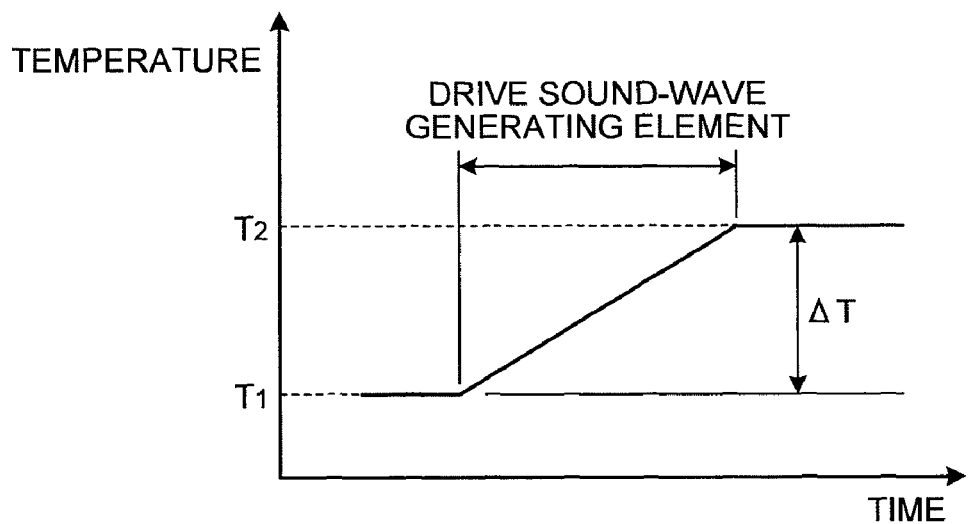
FIG. 6 is a diagram that explains a determination method for determining whether the stirring of the liquid contained in the reaction vessel is successful or unsuccessful on the basis of the temperature of the cleaning water measured by a temperature sensor.

After the cleaning water is stirred for a certain period of time, the control unit 15 measures the temperature (T2) of the cleaning water in the reaction vessel 5 using the temperature signal input from the temperature sensor 36 (step S106). The control unit 15 outputs the measured temperature (T2) of the cleaning water to the determining unit 16. Next, the control unit 15 causes the determining unit 16 to determine whether the stirring is successful or unsuccessful (step S108). As depicted in FIG. 6, the determining unit 16 determines whether the stirring is successful or unsuccessful on the basis of a temperature difference ($\Delta T$) between the temperature (T1) of the cleaning water before the stirring and the temperature (T2) of the cleaning water after the stirring, which have been input from the control unit 15.

Even if the sound-wave generating element 23 of the determining stirrer 28 is correctly operated, the generated sound wave is not propagated to the cleaning water contained in the reaction vessel 5 and the cleaning water is not stirred when, for example, the sound-wave generating element 23 is separated from the reaction vessel. Thus, the temperature of the cleaning water is not increased although the sound-wave generating element 23 is operated. The control unit 15 may determine a threshold ($\Delta Ts$) concerning the temperature difference ($\Delta T$) in advance and stores the threshold ($\Delta Ts$) in the determining unit 16. If the temperature difference ($\Delta T$) is equal to or less than the threshold ($\Delta Ts$) ($\Delta T \leq \Delta Ts$), the control unit 15 causes the determining unit 16 to determine it as a stirring failure.

Next, the control unit 15 rotates the cam 31 of the stirring determining device 30 to raise the arm 34 to a predetermined position and lifts the temperature sensor 36 from the reaction vessel 5 (step S110). The above is the successful/unsuccessful determination of the stirring of the cleaning water using each of the reaction vessels 5, which is performed before the analysis operation is started. The reaction vessel 5, for which the stirring failure is determined, is prevented from being used. The analysis of a specimen is performed by using the other reaction vessel 5, for which the stirring failure is not determined. At that time, the determining unit 16 may output a warning signal relating to an indication, which indicates that the stirring failure is determined, and the position number of the reaction vessel 5 to the display unit 18 via the control unit 15 so that the position of the reaction vessel 5 with the stirring failure is displayed.

As described, if it is determined whether the stirring is successful or unsuccessful before the analysis is started, the reaction vessel 5 with the stirring failure can be removed before the specimen and the reagent are dispensed. Thus, it is possible to prevent the waste of the specimen and the reagent and prevent the output of an incorrect analysis value due to the stirring failure. In the cleaning system 13, the cleaning-water tank 13M is held in the constant-temperature water tank 14 in which the heater 14a is arranged. The cleaning water is controlled at 35 to 45° C., and the reaction table 4 is rotated while the reaction vessel 5 is kept at a predetermined temperature (for example, 37° C.). Therefore, the temperature sensor 36 of the stirring determining device 30 can stably measure the temperature of the cleaning water in the reaction vessel 5 with high accuracy.

The determination of the stirring failure of the liquid on the basis of the temperature measurement of the liquid can be performed after the analysis is finished. In this case, because an analysis result using the reaction vessel 5 for which the stirring failure is determined is not reliable, the control unit 15 displays the indication on the display unit 18 so as to alert an operator to call attention and causes an analysis to be performed again using the different reaction vessel 5 for the analysis item of the same specimen.

Figure 7:
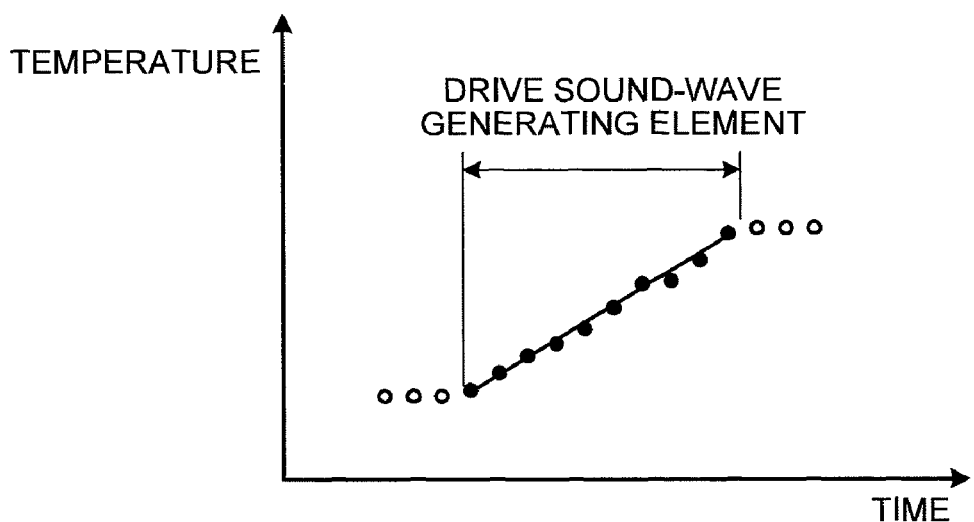
FIG. 7 is a diagram that explains another determination method.

When determining whether the stirring is successful or unsuccessful, the temperature of the cleaning water may be measured at certain time intervals plural times so as to set in advance a threshold (ks) concerning a gradient of a regression line of the time and the temperature of cleaning water as depicted in FIG. 7, while driving the sound-wave generating element 23. A stirring failure is determined by comparing the result with the actually measured gradient (k) of the regression line. It is also possible to determine whether the stirring is successful or unsuccessful based on a threshold concerning the temperature change that is set using a curve approximation based on a hyperbolic function, an exponent function, or a logarithmic function, instead of a straight-line approximation.

Furthermore, the tip end of the overflow suction nozzle 13c of the cleaning nozzle pair 13F may be lowered so as to reduce the amount of cleaning water used for the successful/unsuccessful determination of the stirring. With this, the temperature increase upon stirring at the same electric power becomes large.

Second Embodiment

Next, a detailed explanation will be given of a second embodiment of the stirring determining device, the stirring determining method, and the analyzer according to the present invention with reference to the attached drawings. In the first embodiment, the position for stirring the liquid is the same as the position for measuring the temperature of the liquid. In the second embodiment, the position for stirring the liquid is different from the position for measuring the temperature of the liquid.

Figure 8:
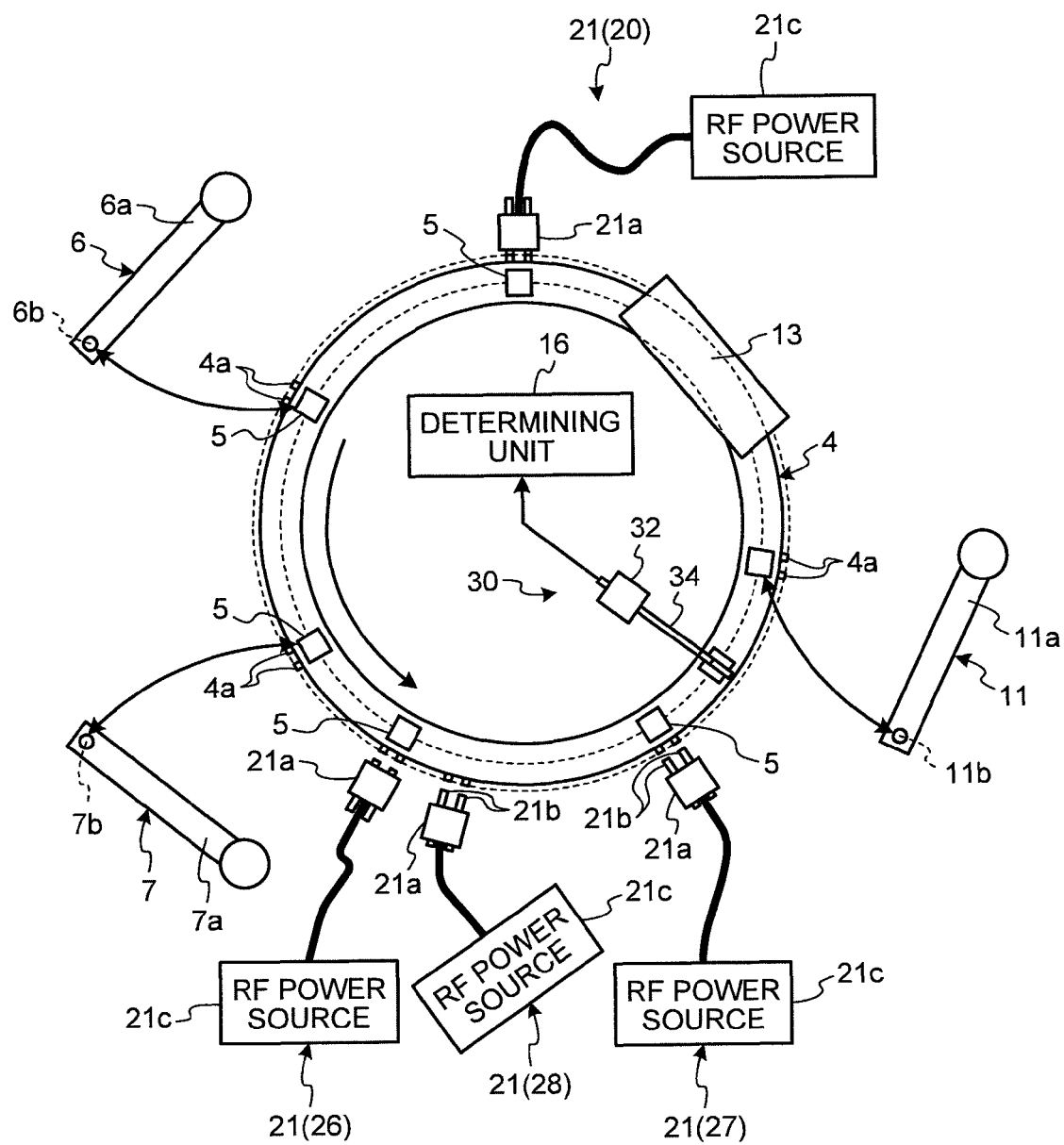
FIG. 8 is a plain view that illustrates reagent dispensing systems, a specimen dispensing system, a specimen stirrer, reagent stirrers, a determining stirrer, and a stirring determining device arranged near the reaction table in an automatic analyzer according to a second embodiment.
Figure 9:
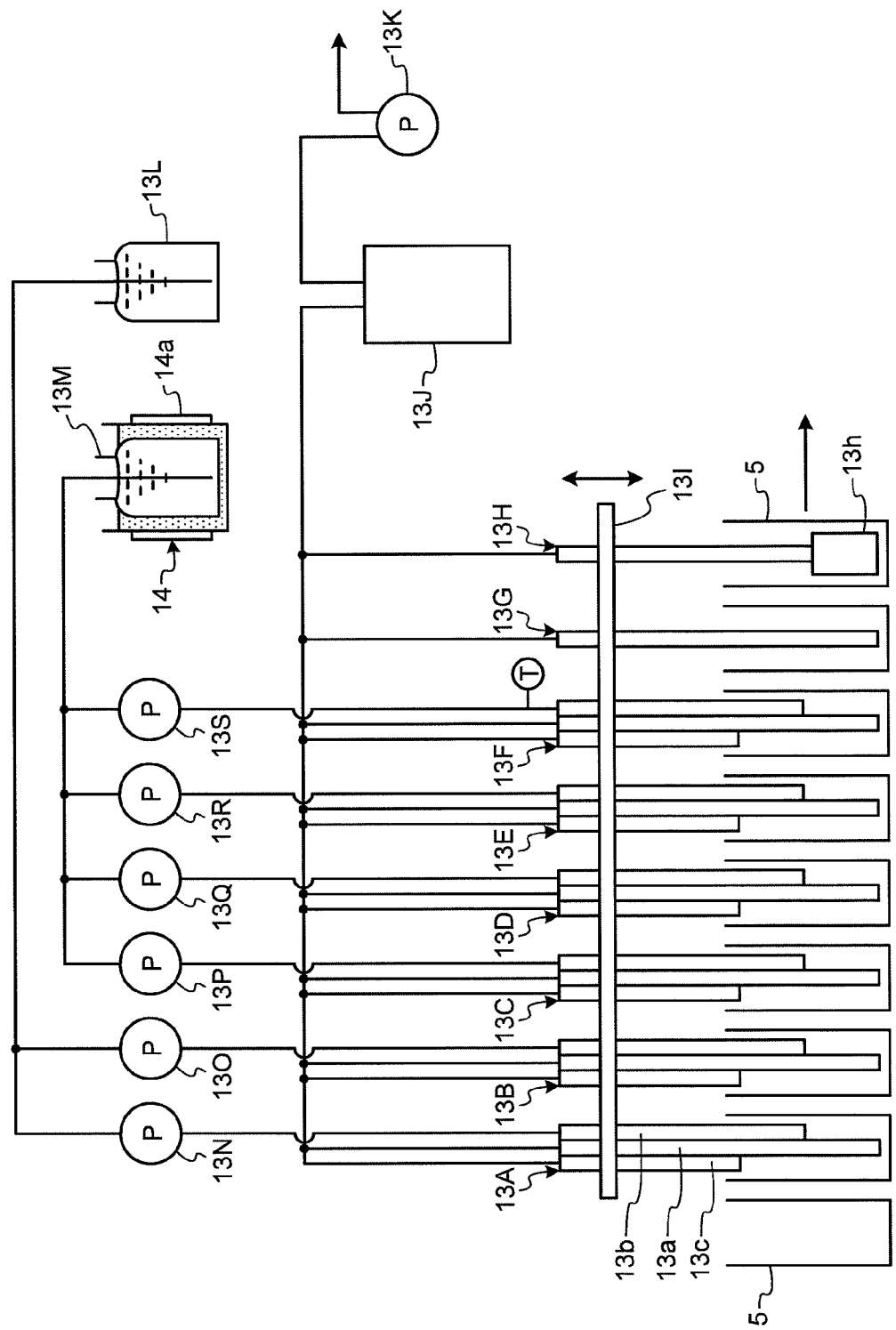
FIG. 9 is a schematic configuration diagram that illustrates a cleaning system used in the automatic analyzer according to the second embodiment.

FIG. 8 is a plain view that illustrates reagent dispensing systems, a specimen dispensing system, a specimen stirrer, reagent stirrers, a determining stirrer, and a stirring determining device arranged near a reaction table in an automatic analyzer according to the second embodiment. FIG. 9 is a schematic configuration diagram that illustrates a cleaning system used in the automatic analyzer according to the second embodiment. Because the automatic analyzers according to the second embodiment and a subsequent embodiment have the same basic configuration that includes the stirring determining device as the automatic analyzer according to the first embodiment, the same reference numerals are used for the same components.

In the automatic analyzer according to the second embodiment, as depicted in FIG. 8, the determining stirrer 28 is located near the reagent stirrer 26, and the position where the determining stirrer 28 stirs the cleaning water in the reaction vessel 5 upon determining whether the stirring is successful or unsuccessful is different from the positions where the temperatures (T1, T2) of the cleaning water are measured. Specifically, as depicted in FIG. 9, in the cleaning system 13 used in the automatic analyzer according to the second embodiment, a temperature sensor T, such as a thermistor or a thermocouple, is arranged near the dispensing nozzle 13b on a pipe that sends cleaning water to the dispensing nozzle 13b of the cleaning nozzle pair 13F. In the same manner as the automatic analyzer according to the first embodiment, before the analysis is started or after the analysis is finished, the automatic analyzer according to the second embodiment determines whether the stirring is successful or unsuccessful, independently of the analysis operation. The temperature (T1) of the cleaning water, which is discharged into the reaction vessel 5, is measured at the position of the cleaning system 13 before the stirring.

In the second embodiment, the reaction table 4 moves the reaction vessel 5 that is a stirring target to the position of the cleaning nozzle pair 13F of the cleaning system 13 under the control of the control unit 15. Next, after the control unit 15 causes a certain amount of cleaning water to be discharged into the reaction vessel 5 from the dispensing nozzle 13b, the control unit 15 causes the support member 13I to move up the cleaning nozzle pair 13F together with other nozzle pairs. Then, the control unit 15 rotates the reaction table 4 so as to move the reaction vessel 5 to the position of the determining stirrer 28 and causes the determining stirrer 28 to stir the cleaning water in the reaction vessel 5.

After the stirring, the control unit 15 rotates the reaction table 4 so as to move the reaction vessel 5 that is a stirring target to the position of the temperature sensor 36 of the stirring determining device 30 and causes the temperature sensor 36 to measure the temperature (T2) after the stirring. The determining unit 16 then determines whether the stirring is successful or unsuccessful on the basis of the temperature difference ($\Delta T = T2 - T1$) between the temperature (T1) of the cleaning water before the stirring and the temperature (T2) of the cleaning water after the stirring, which is measured by the temperature sensor 36, by comparing the temperature difference with the certain threshold $\Delta Ts$ set in advance. After the temperature (T2) is measured, the cleaning water in the reaction vessel 5 is sucked up by the cleaning system 13.

Even if the same stirring energy is applied to the cleaning water by the determining stirrer 28 upon the stirring, the increased temperature is different depending on the temperature (T1) before the stirring, and the temperature difference ($\Delta T = T2 - T1$) can be different. Therefore, for example, as indicated in Table 1, the threshold $\Delta Ts$ is set in advance concerning the temperature difference ($\Delta T = T2 - T1$) for each range of the temperature (T1) before the stirring and is stored in the determining unit 16. If the temperature difference ($\Delta T$) is equal to or less than the threshold $\Delta Ts$ ($\Delta T \leq \Delta Ts$), the determining unit 16 determines it as a stirring failure. In this manner, the automatic analyzer according to the second embodiment can further improve the accuracy of the successful/unsuccessful determination of the stirring performed by the determining unit 16 compared to the automatic analyzer according to the first embodiment.

TABLE 1

| Condition | $\Delta Ts$ | Remarks |
|---|---|---|
| $T_1 < 35$ | — | Determine as cleaning-water temperature control error |
| $35 \leq T_1 < 36$ | 0.9 | |
| $36 \leq T_1 < 37$ | 0.89 | |
| $37 \leq T_1 < 38$ | 0.86 | |
| $38 \leq T_1 < 39$ | 0.83 | |
| $39 \leq T_1 < 40$ | 0.8 | |
| $40 \leq T_1 < 41$ | 0.77 | |
| $41 \leq T_1 < 42$ | 0.73 | |
| $42 \leq T_1 < 43$ | 0.69 | |
| $43 \leq T_1 < 44$ | 0.64 | |
| $44 \leq T_1 < 45$ | 0.6 | |
| $45 < T_1$ | — | Determine as cleaning-water temperature control error |

When the position for stirring the cleaning water is different from the position for measuring the temperature, the automatic analyzer has an advantage in that the design flexibility for arranging the determining stirrer 28 and the stirring determining device 30 is increased.

The determining unit 16 may determine whether the stirring is successful or unsuccessful by comparing the temperature difference ($\Delta T=T2-T1$) with the single threshold $\Delta Ts$ in the same manner as the first embodiment.

Third Embodiment

Next, a detailed explanation will be given of a third embodiment of the stirring determining device, the stirring determining method, and the analyzer according to the present invention with reference to the attached drawings. In the first embodiment, the temperature sensor is supported by the arm that moves up and down. In the third embodiment, the temperature sensor moves up and down with the cleaning system.

Figure 10:
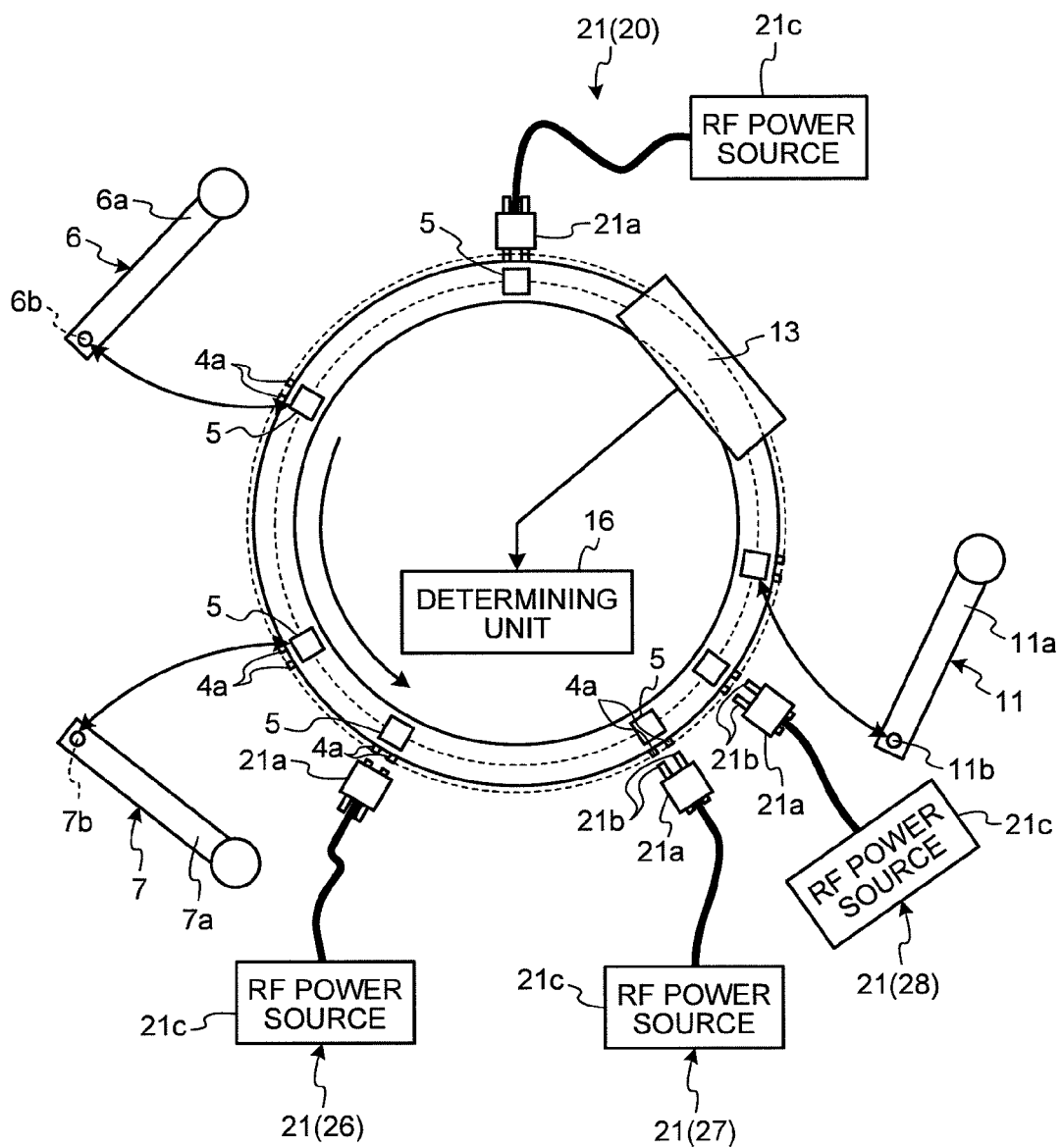
FIG. 10 is a plain view that illustrates reagent dispensing systems, a specimen dispensing system, a specimen stirrer, reagent stirrers, a determining stirrer, and a stirring determining device arranged near the reaction table in an automatic analyzer according to a third embodiment.
Figure 11:
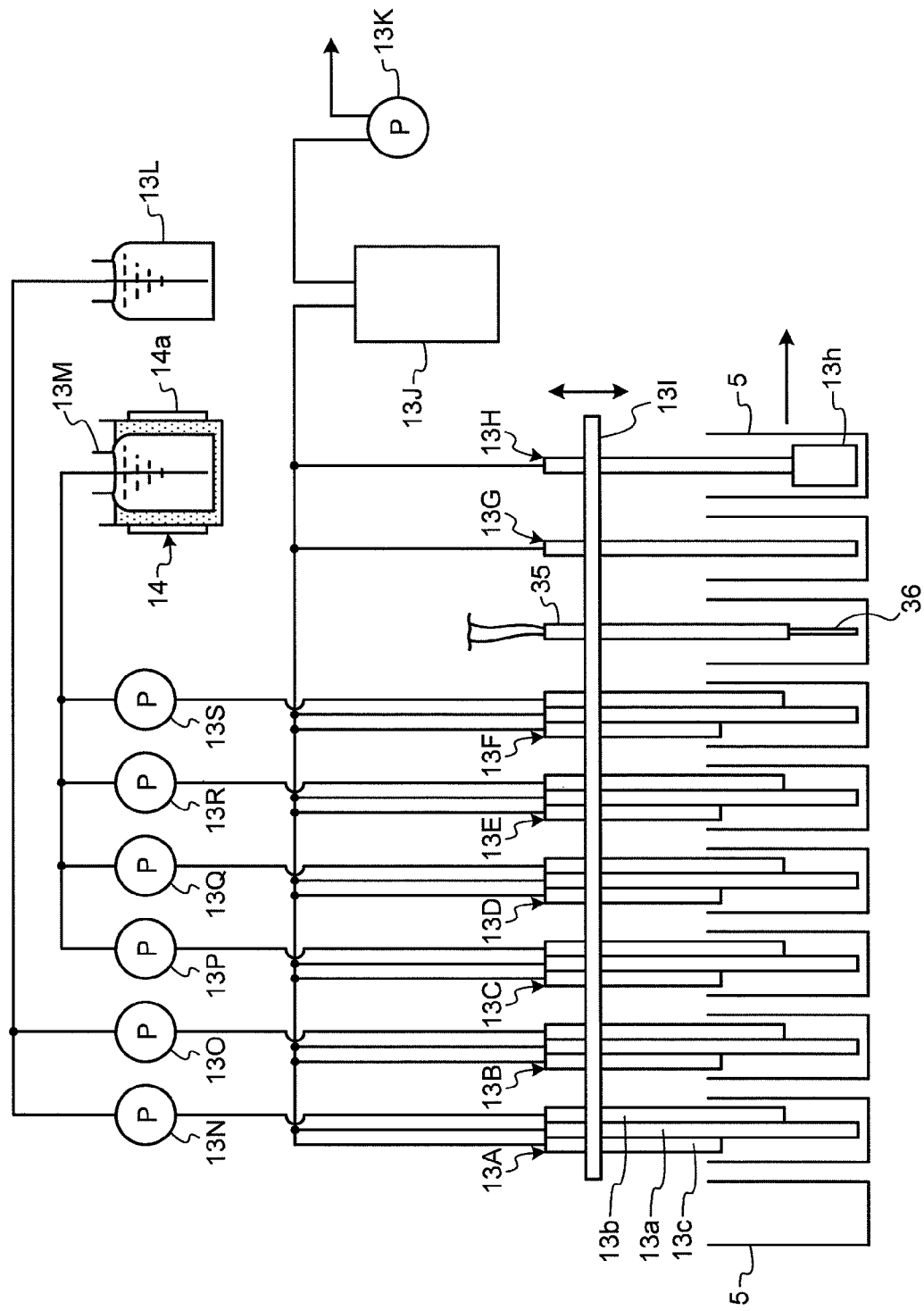
FIG. 11 is a schematic configuration diagram that illustrates a cleaning system used in the automatic analyzer according to the third embodiment.

FIG. 10 is a plain view that illustrates reagent dispensing systems, a specimen dispensing system, a specimen stirrer, reagent stirrers, a determining stirrer, and a stirring determining device arranged near a reaction table in an automatic analyzer according to the third embodiment. FIG. 11 is a schematic configuration diagram that illustrates a cleaning system used in the automatic analyzer according to the third embodiment.

As depicted in FIG. 10, the stirring determining device 30 is not provided in the automatic analyzer according to the third embodiment. In place of the stirring determining device 30, as depicted in FIG. 11, the automatic analyzer according to the third embodiment has the support member 35 equipped with the temperature sensor 36 attached to its lower end. The support member 35 is arranged between the cleaning nozzle pair 13F and the suction nozzle 13G of the cleaning system 13 and supported by the support member 13I.

The automatic analyzer according to the third embodiment measures the temperature (T1) of the cleaning water discharged into the reaction vessel 5 using the temperature sensor 36 arranged in the cleaning system 13. Then, the reaction table 4 is rotated to move the reaction vessel 5 and the cleaning water in the reaction vessel 5 is stirred by the determining stirrer 28. When the reaction table 4 is further rotated to move the reaction vessel 5 that is the stirring target to the position of the temperature sensor 36 of the cleaning system 13, the temperature (T2) of the cleaning water after the stirring is measured by the temperature sensor 36. The determining unit 16 then compares the temperature difference ($\Delta T=T2-T1$) between the temperature (T1) of the cleaning water before the stirring and the temperature (T2) of the cleaning water after the stirring with the certain threshold $\Delta Ts$ set in advance in order to determine whether the stirring is successful or unsuccessful.

In the automatic analyzer according to the third embodiment, the temperature sensor 36 is arranged in the cleaning system 13 instead of the stirring determining device 30. Therefore, the stirring determining device 30 that moves the temperature sensor 36 up and down does not need to be arranged in the automatic analyzer according to the third embodiment. Thus, there is an advantage in that design flexibility is increased for arranging other members or devices.

In the first and second embodiments, the support rod 32 and the temperature sensor 36 are moved up and down by the cam 31 in the stirring determining device 30, but the configuration is not limited to the cam 31. For example, the temperature sensor 36 can be moved up and down using a linear slide, a ball screw, or the like.

The automatic analyzer according to the present invention can be applied to an automatic analyzer for any of a biochemical system, an immune system, and a gene system. In an automatic analyzer for a gene system, a reaction vessel is a disposable type; however, in this case, it is possible that, before a specimen is dispensed into each reaction vessel and analysis is performed, the cleaning water is discharged into a reaction vessel, and, after it is confirmed that the stirring is performed successfully, the cleaning water is sucked up and removed and then the analysis is performed.

In the present invention, the temperature of the cleaning water before and after the stirring, which is measured each time the cleaning water contained in each reaction vessel is stirred, may be stored in the control unit 15, and the occurrence of a stirring failure may be predicted using a time-course record of the temperature of the cleaning water in each reaction vessel, or it can be used for improving the determination accuracy upon determining whether the stirring is successful or unsuccessful.

The automatic analyzer according to the present invention dispenses the cleaning water, which is liquid used for the temperature measurement, by the cleaning system upon determining whether the stirring is successful or unsuccessful. A dispensing means that is a syringe pump may be used in order to improve the dispensing accuracy of the cleaning water.

Furthermore, the above embodiment uses the wired system, in which the connecting terminal 21b of the electric-power transmitting member 21 is brought into contact with the connecting terminal 4a arranged on the outer surface of the reaction table 4 using the solenoid 21a so as to drive the sound-wave generating element 23. However, the stirring determining method according to the present invention can be used in the case where the electric-power transmitting member 21 wirelessly supplies the electric power to the sound-wave generating element 23, and it can be determined whether the stirring is successful or unsuccessful with higher accuracy than the case where a reflected signal from the sound-wave generating element 23 is detected.

Although the case is explained where the automatic analyzer described in the embodiments includes one reaction table 4, i.e., one analysis unit, an automatic analyzer may be configured to have a plurality of analysis units. Although the case is explained where the two reagent tables for the first reagent and the second reagent are arranged, an automatic analyzer can include one reagent table.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An analyzer comprising:
a specimen dispensing system configured to dispense a specimen to a vessel; and
an analysis optical system configured to emit analysis light to analyze the specimen in the reaction vessel; and
a stirrer that stirs a liquid contained in the vessel using a sound wave generated by a sound-wave generating unit attached to the vessel; and
a cleaning system that cleans the vessel; and
a stirring determining device that determines whether stirring by the stirrer is successful or unsuccessful, the stirring determining device comprising:

a temperature sensor that measures a temperature of the liquid, wherein the temperature sensor is arranged in the cleaning system; and a determining unit that determines whether stirring of the liquid contained in the vessel is successful or unsuccessful depending on the temperature of the liquid measured at least before and after the stirring by the temperature sensor, wherein the cleaning system is configured to clean the reaction vessel after the analysis optical system finishes analyzing the specimen.

2. A stirring determining device that determines whether stirring by the stirrer, which stirs a liquid contained in the vessel of the analyzer of claim 1 using a sound wave generated by a sound-wave generating unit that is attached to the vessel, is successful or unsuccessful, the stirring determining device comprising:

a temperature sensor that measures a temperature of the liquid; and a determining unit that determines whether stirring of the liquid contained in the vessel is successful or unsuccessful depending on the temperature of the liquid measured at least before and after the stirring by the temperature sensor.

3. A stirring determining method for determining whether stirring by the stirrer, which stirs a liquid contained in the vessel of the analyzer of claim 1 using a sound wave generated by a sound-wave generating unit, is successful or unsuccessful, the stirring determining method comprising:

a temperature measuring step of measuring a temperature of the liquid; and a determining step of determining whether stirring of the liquid contained in the vessel is successful or unsuccessful depending on the temperature of the liquid.

4. The stirring determining method according to claim 3, wherein an amount of the liquid and the temperature of the liquid before the stirring are controlled within a predetermined range.

5. The analyzer according to claim 1, wherein a position where the temperature sensor measures the temperature of the liquid contained in the vessel is same as a position where the stirrer stirs the liquid contained in the vessel.

6. The analyzer according to claim 1, wherein a position where the temperature sensor measures the temperature of the liquid contained in the vessel is different from a position where the stirrer stirs the liquid contained in the vessel.

7. The analyzer according to claim 1, wherein the liquid is cleaning water supplied by the cleaning system.

8. The analyzer according to claim 7, further comprising a control unit that controls an operation of the cleaning system such that an amount of the cleaning water supplied to the vessel upon determining whether the stirring of the liquid is successful or unsuccessful is smaller than an amount of the cleaning water supplied to the vessel upon cleaning.

9. The analyzer according to claim 1, wherein determination as to whether stirring of the liquid is successful or unsuccessful in accordance with temperature measurement of the liquid is performed before analysis is started or after analysis is finished.

10. The analyzer according to claim 1, wherein the cleaning system includes detergent nozzle pairs, cleaning nozzle pairs, suction nozzles, a waste-liquid tank, a detergent tank, a cleaning water tank, and liquid sending pumps that are all connected via pipes.

11. The analyzer according to claim 10, wherein the temperature sensor is attached to a support member arranged between the cleaning nozzle pair and the suction nozzle of the cleaning system.

* * * * *